United States Patent [19]

Engelbrecht et al.

[11] Patent Number: 4,538,305
[45] Date of Patent: Sep. 3, 1985

[54] ARTICULATED PROSTHESIS

[75] Inventors: Eckart Engelbrecht, Hamburg; Elmar Nieder, York; Arnold Keller, Kaihude, all of Fed. Rep. of Germany

[73] Assignees: GMT Gesellschaft für medizinische Technik mbH; Waldemar Link GmbH & Co., both of Hamburg, Fed. Rep. of Germany

[21] Appl. No.: 398,638

[22] Filed: Jul. 15, 1982

[30] Foreign Application Priority Data

May 19, 1981 [DE] Fed. Rep. of Germany ....... 3119841

[51] Int. Cl.³ .............................................. A61F 1/00
[52] U.S. Cl. .................................... 623/20; 128/92 C; 623/18
[58] Field of Search ........................ 3/1.9, 1.91, 1.911; 128/92 C

[56] References Cited

U.S. PATENT DOCUMENTS 3,934,272 1/1976 Wearne et al. ...................... 3/1.911
4,094,017 6/1978 Matthews et al. .................... 3/1.911
4,112,522 9/1978 Dadurian et al. ..................... 3/1.91

OTHER PUBLICATIONS

Matthews et al, "Spherocentric Knee", Clinical Orthopaedics, No. 94, Jul.-Aug. 1973, pp. 234-240.

Primary Examiner—Richard J. Apley
Assistant Examiner—David J. Isabella
Attorney, Agent, or Firm—Peter K. Kontler

[57] ABSTRACT

A prosthesis for the knee joint has a tibial component and a femoral component. No mechanical connection exists between these components. The tibial component includes a shaft which carries a platform and is received in the cavity of the tibia so as to position the tibial component. The platform supports a bearing element which engages the femoral component and, in addition, a projection is mounted on the platform and extends towards the femoral component. The femoral component includes a shaft which carries a hinge and is received in the cavity of the femur to position the femoral component. The hinge, which defines a pivot axis for bending of the knee, comprises a hinge pin having a recess which faces the tibial component. The projection is slidably received in the recess and defines a rotational axis about which limited rotation of the tibial component relative to the femoral component may take place. In addition, the projection maintains the hinge pin in requisite position. The prosthesis is economical and may be constructed in a simple manner, without any screw connections, from elements which are readily assembled.

9 Claims, 13 Drawing Figures

ARTICULATED PROSTHESIS

BACKGROUND OF THE INVENTION

The invention relates generally to a prosthesis for use at a joint.

More particularly, the invention relates to an internal or implanted prosthesis for use at a joint.

A known internal prosthesis for use at a knee has a femoral and a tibial component which are not connected with one another. At least one bearing is arranged between the two components and permits the latter to undergo pivotal movements relative to one another about an axis extending transversely of the components and to undergo rotational movements relative to one another about an axis extending longitudinally of the components.

An internal prosthesis of this type has been found in practice to yield satisfactory results for the user. The implanted knee joint enables the user to perform movements which closely approximate those possible with the natural knee joint. In fact, there have been instances where users have participated in sports such as, for example, skiing, which emphasize the legs without being hindered by the prosthesis.

The success of the prosthesis makes it desirable to simplify the manufacture thereof. It is further desirable to simplify the implantation of the prosthesis.

OBJECTS AND SUMMARY OF THE INVENTION

It is an object of the invention to provide an articulated prosthesis which may be manufactured more readily than heretofore.

Another object of the invention is to provide an articulated prosthesis which may be manufactured more economically than heretofore.

An additional object of the invention is to provide an internal prosthesis which may be implanted more easily than heretofore.

It is also an object of the invention to provide an internal prosthesis of the type outlined above which is designed so that the relatively movable components, e.g. a femoral component and a tibial component in the case of prosthesis for a knee, are held in engagement in a simpler manner than heretofore.

A concomitant object of the invention is to provide an internal prosthesis of the type outlined above which is designed so that the engagement between the relatively movable components, e.g. a femoral component and a tibial component in the case of a prosthesis for a knee, is enhanced by means of high-strength structural elements.

The preceding objects, as well as others which will become apparent as the description proceeds, are achieved by the invention.

One aspect of the invention resides in an articulated prosthesis, particularly an internal prosthesis, which comprises a pair of components arranged to be situated on opposite sides of a joint and to engage corresponding parts of the anatomy. A hinge is mounted on one of the components and permits pivotal movement of the components relative to one another about a first axis. The hinge includes a hinge pin which is guided by the other of the components so as to permit relative rotation of the latter and the pin about a second axis transverse to the first axis.

In the case of a prosthesis for a knee, one of the components may be a femoral component and the other of the components may be a tibial component.

According to a preferred embodiment of the invention, the first or pivot axis extends transversely of the components while the second or rotational axis extends longitudinally thereof.

It is further preferred for the relatively movable components to be unconnected.

The prosthesis of the invention may be assembled using structural elements which have been successfully incorporated in conventional prostheses of the hinge type, that is, prostheses which permit relative movement of the components only about a single axis. Such structural elements have been found to be extraordinarily resistant to the stresses which are normally encountered. Furthermore, since prostheses of the hinge type are familiar to many physicians, good results can be expected when implanting a prosthesis in accordance with the invention. Although the prosthesis of the invention may incorporate the structural elements used in conventional hinge prostheses and also exhibits many of the advantages of such prostheses, the prosthesis according to the invention nevertheless enables a major disadvantage of conventional hinged prostheses to be overcome in that the relatively movable components are able to pivot as well as rotate relative to one another about mutually transverse axes. In this regard, the hinge pin in the prosthesis of the invention may be mounted for rotation in a simple manner. This makes it possible for the prosthesis to be manufactured economically and further simplifies implantation of the prosthesis.

In accordance with an advantageous embodiment of the invention, the hinge pin is mounted for rotation by forming the same with a recess and forming the other component with a rod-like projection which extends into the recess. This arrangement makes use of the established principle employed in conventional internal prostheses of the type which permit relative pivotal as well as rotational movements of the components about mutually transverse axes and enables a large degree of bending to be achieved. Moreover, the projection may be relatively long so that it has a relatively large external surface area. This makes it possible for the projection to carry a relatively large load at a relatively low stress, that is, at a relatively low load per unit area. In addition, the prosthesis of the invention permits the hinge to be designed with a hinge pin which is relatively thick in comparison to the small space available for the prosthesis. As a result, the hinge pin may provide sufficient support for the projection to enable the prosthesis to withstand even exceptionally high impact loads.

In the case of a prosthesis for use in a knee, it is preferred for the hinge to be mounted on the femoral component and for the projection to be mounted on the tibial component.

The novel features which are considered as characteristic of the invention are set forth in particular in the appended claims. The improved prosthesis itself, however, both as to its construction and its mode of operation, together with additional features and advantages itself, will be best understood upon perusal of the following detailed description of certain specific embodiments with reference to the accompanying drawing.

DESCRIPTION OF THE PREFERRED EMBODIMENTS

Figure 1:
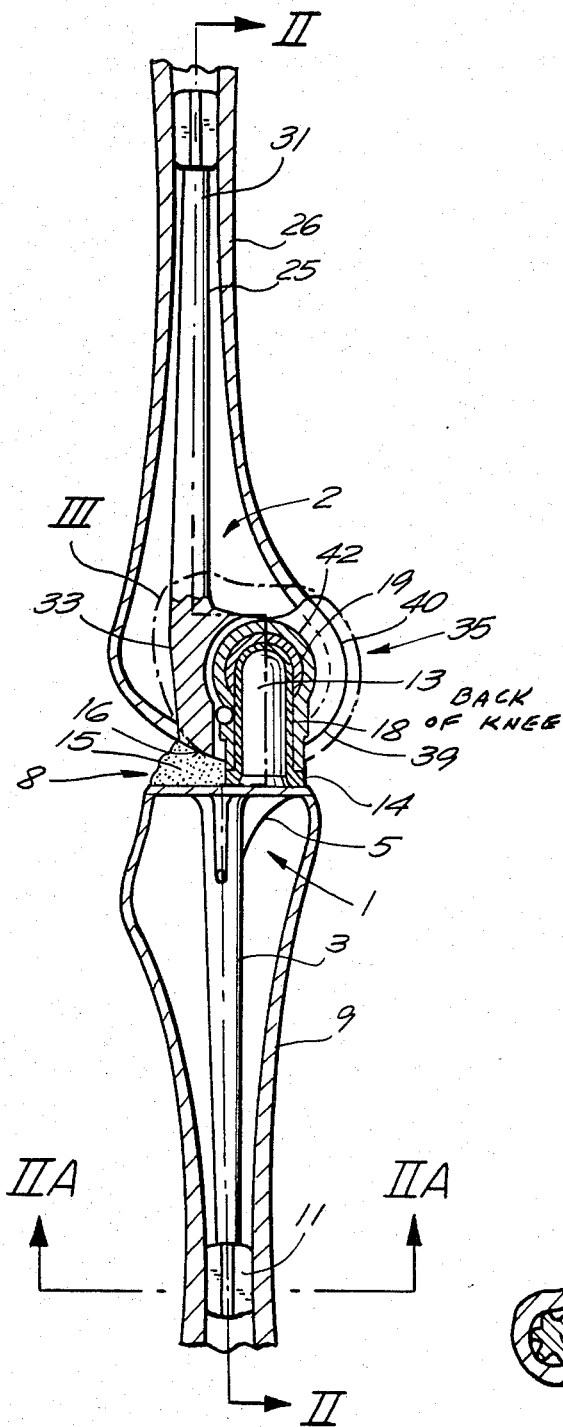
FIG. 1 is a longitudinal sectional side view through a femur and tibia showing a prosthesis according to the invention implanted at a knee.
Figure 2A:
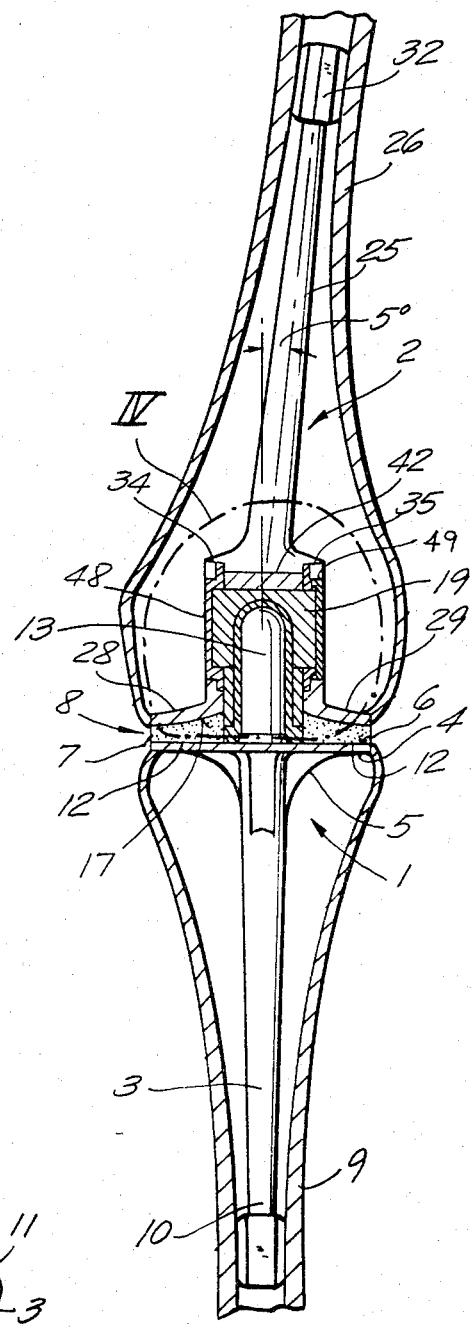
FIG. 2A is a cross-sectional view in the direction of the arrows IIA—IIA of FIG. 1.
Figure 2:
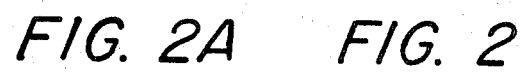
FIG. 2 is a cross-sectional view in the direction of the arrows II—II of FIG. 1.

The invention will be described with reference to a prosthesis to be implanted in a knee and, in this regard, FIGS. 1 and 2 illustrate a femur 26 and a tibia 9. It will be understood, however, that the prosthesis of the invention may find application at joints other than a knee.

As further illustrated in FIGS. 1 and 2, the prosthesis according to the invention includes a tibial component 1 and a femoral component 2.

Figure 6:
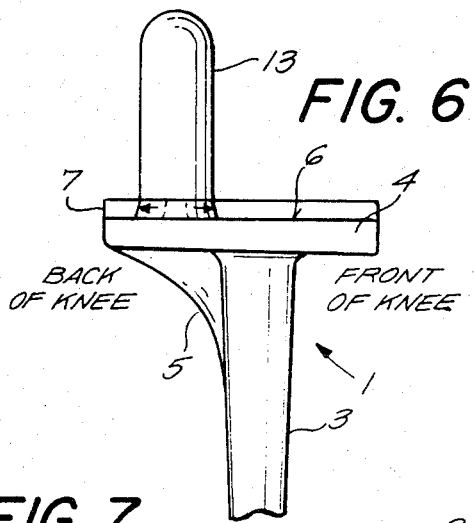
FIG. 6 is a schematic side view of the tibial component of the prosthesis according to the invention.

Referring now to FIG. 6 in conjunction with FIGS. 1 and 2, it may be seen that the tibial component 1 comprises a shaft 3 which supports a platform 4. The shaft 3 is connected with the platform 4 at approximately the center of gravity of the latter. Ribs 5 extend between the shaft 3 and the platform 4 in order to stiffen the tibial component 1.

The tibia 9 narrows in a direction away from the platform 4, and the shaft 3 has an end 10 which is inserted in the narrow portion of the tibia 9. The shaft 3 converges conically in a direction from the platform 4 to the end 10. As best seen in FIGS. 1, 2 and 2A, a cap 11 is mounted on the end 10 of the shaft 3. The cap 11 serves to guide the shaft 3 in the narrow portion of the tibia 9.

With reference still to FIGS. 1, 2 and 6, the platform 4 has a planar upper surface 6. An upstanding rim 7 is provided at the outer edges of the platform 4 and at least partly surrounds the upper surface 6. A rod-like projection 13 of circular cross section extends upwardly from the upper surface 6. The projection 13 has a free end remote from the platform 4 and this end of the projection 13 is hemispherical. The projection 13 may taper conically in a direction from its free end towards the platform 4. The projection 13 is perpendicular to the upper surface 6 of the platform 4.

As most clearly shown in FIGS. 1 and 6, the projection 13 is arranged in the region of the platform 4 adjacent the rear of the knee. In other words, the projection 13 is arranged in the region of the platform 4 which is situated adjacent the inner radius of the bend defined when the knee is bent. FIG. 2 illustrates that the projection 13 is centrally positioned on the platform 4 as considered in a direction across the knee, that is, in a direction from the left-hand to the right-hand side of the knee or vice versa.

A support or bearing element 8 is arranged on the platform 4 and serves to absorb compressive stresses transmitted between the tibial component 1 and the femoral component 2. The support 8, which has a planar lower surface resting on the upper surface 6 of the platform 4, is prevented from moving by the rim 7. The support 8 has a generally circular outline which is interrupted in the region of the projection 13 by a cutout 14. The cutout 14 extends to the edge of the support 8 so that the latter resembles a horseshoe with a pair of legs 12 as seen in plan view. The projection 13 passes through the cutout 14 and, as best seen in FIGS. 2 and 4, is flanked by the legs 12.

Figure 4:
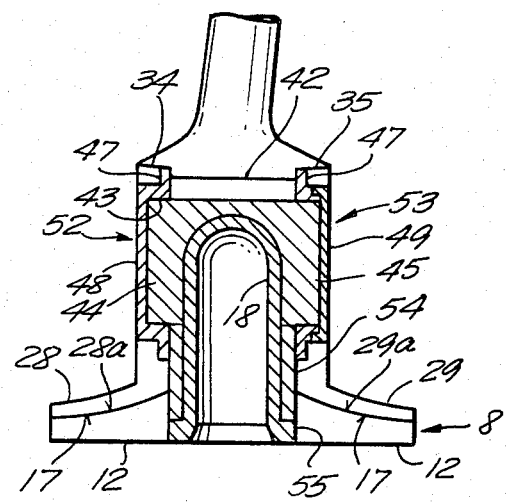
FIG. 4 is an enlarged view of the area IV of FIG. 2 showing additional details of the bearing member and hinge of FIG. 3.

As also shown in FIGS. 2 and 4, the legs 12 have upwardly facing bearing surfaces 17. The bearing surfaces 17 are curved in a direction transverse to the legs 12. The curvature of the bearing surfaces 17 is such that the thickness of the legs 12 increases in a direction from the rim 7 towards the projection 13. As will be explained more fully below, the femoral component 2 rides on the bearing surfaces 17 and the latter are designed so as not to interfere with relative pivotal movement of the tibial component 1 and the femoral component 2 resulting in bending of the knee.

Referring to FIG. 1, the support 8 further includes a bridging portion 15 which merges into the legs 12 and connects the same. The bridging portion 15 is located in front of the legs 12 and the projection 13 as considered in a direction from the front of the knee towards the back. The bridging portion 15 has an upwardly facing bearing surface 16 which extends from one of the legs 12 to the other and is symmetrically arranged with respect to the legs 12. The bearing surface 16, which has somewhat of an inclination, is located at a level above the bearing surfaces 17 of the legs 12 and merges into the bearing surfaces 17 via faces of the support 8 which are configurated so as not to interfere with relative pivotal movement of the tibial component 1 and the femoral component 2 resulting in bending of the knee. The bridging portion 15 descends relatively steeply in a direction from the bearing surface 16 towards the rim 7.

With reference to FIGS. 1-4, the femoral component 2 includes a pair of spaced bearing members 34 and 35 which are mounted on a plate 33. The plate 33 further carries a shaft 25 which assists in positioning the femoral component 2 in the femur 26 in the same fashion as the shaft 3 of the tibial component 1 assists in positioning the latter in the tibia 9. The femur 26 narrows on a direction upwards from the plate 33 and the bearing members 34,35, and the shaft 25 has a free end 31 which projects into the narrow portion of the femur 26. A cap 32 is screwed on to the free end 31 of the shaft 25 and is similar to the cap 11 provided on the shaft 3 of the tibial component 1. As is the case for the cap 11, the cap 32 serves to guide the shaft 25 in the femur 26. The shaft 25 converges conically in a direction from the plate 33 towards the free end 31 in the same manner as the shaft 3 of the tibial component 1 converges conically in a direction from the platform 4 towards the free end 10 of the shaft 3.

The shaft 25 joins the plate 33 centrally of the bearing members 34 and 35. As indicated in FIG. 2, the shaft 25 is mounted on the plate 33 in such a manner that it is inclined to the vertical by approximately 5 degrees. This inclination corresponds approximately to the physiological valgus of the knee joint. This physiological valgus is taken into consideration by inclining the shaft 25 in the direction of the femur 26 which extends into the pelvis at an angle.

Figure 3:
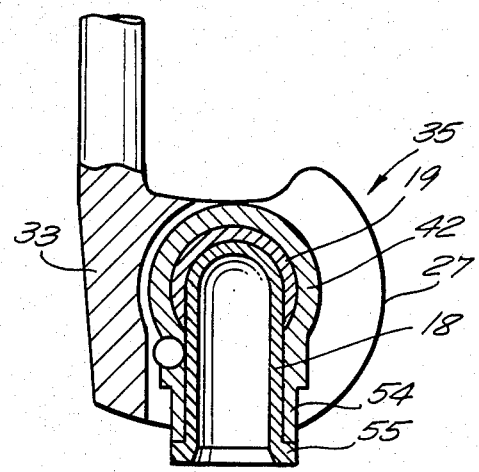
FIG. 3 is an enlarged view of the area III of FIG. 1 illustrating the bearing member and hinge constituting part of the femoral component of the prosthesis in accordance with the invention.
Figure 5:
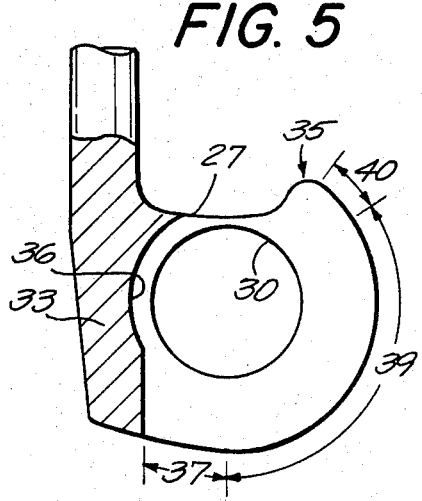
FIG. 5 is a view similar to FIG. 3 but illustrating only the bearing member.

As illustrated in FIG. 5, each of the bearing members 34 and 35 is provided with an opening 30. The openings 30 of the bearing members 34 and 35 are aligned and serve to support a hinge pin 19 in a manner still to be desired. The hinge pin 19 defines a pivot axis extending transversely of the knee, that is, in a direction from the left-hand to the right-hand side of the knee, and permits the knee to be bent. FIGS. 1, 3 and 5 show that the shaft 25 joins the plate 33 immediately in front of the openings 30 in the bearing members 34,35 as considered in a direction from the front of the knee towards the rear. This arrangement is advantageous since it insures that the forces transmitted through the shaft 25 enter the hinge comprising the plate 33, the bearing members 34,35 and the hinge pin 19 immediately in front of the pivot axis defined by the hinge pin 19.

Figure 8:
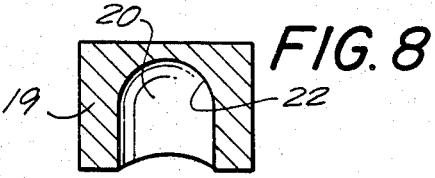
FIG. 8 is a view in the direction of the arrows VIII—VIII of FIG. 7.
Figure 7:
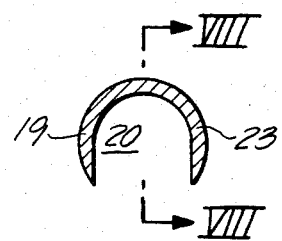
FIG. 7 is a cross-sectional side view of the hinge pin for the prosthesis according to the invention.

A recess 20 shown in FIGS. 7 and 8 is formed in the middle of the hinge pin 19 and is downwardly open. The recess 20 extends transversely to the longitudinal axis of the hinge pin 19. The recess 20 is generally cylindrical but has a hemispherical inner end 22.

Figure 9:
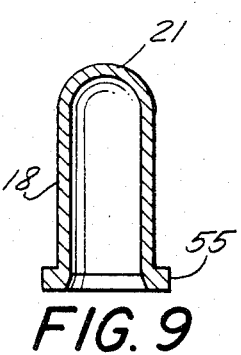
FIG. 9 is a longitudinal cross-sectional view of a sleeve-like member for use with the hinge in the prosthesis in accordance with the invention.

A sheath or sleeve-like member 18 composed of a synthetic plastic material is fixedly mounted in the recess 20 as illustrated in FIGS. 1-4. The recess 20 is sufficiently deep to provide good support for the sheath 18. With reference to FIG. 9, it may be seen that the sheath 18 is generally cylindrical but has a hemispherical end 21. The hemispherical end 21 of the sheath 18 conforms to and engages the hemispherical end 22 of the recess 20.

As illustrated in FIGS. 1-4, the projection 13 which, as mentioned earlier, is normal to the upper surface 6 of the platform 4, extends into the sheath 18. The sheath 18 uniformly engages the entire projection 13 including the hemispherical free end of the latter which conforms to the hemispherical end 21 of the sheath 18. The sheath 18 functions as a bushing which permits the projection 13 and the hinge pin 19 to rotate relative to one another about the longitudinal axis of the projection 13. The projection 13 thus defines an axis of rotation which is perpendicular to the pivot axis defined by the hinge pin 19.

Referring once more to FIG. 7, it is pointed out that the hinge pin 19 is designed in such a manner that the wall 23 which bounds the recess 20 is sufficiently thick to absorb the forces transmitted to the hinge pin 19 by the projection 13. Such forces arise when the tibial component 1 and the femoral component 2 are moved relative to one another into a predetermined position and are due to the fact that the components 1 and 2 must be maintained in this position. In contrast to these positioning forces which are transmitted between the tibial component 1 and the femoral component 2 via the projection 13 and the hinge pin 19, compressive forces in the femoral component 2 are transmitted directly to the bearing surfaces 16 and 17 of the tibial component 1 by the plate 33 and the bearing members 34,35 of the femoral component 2.

In this regard, the bottom surface of the plate 33 seats on the bearing surface 16 when the prosthesis is in a straightened position as may be observed from FIG. 1. The bearing surface 16 serves not only for the transmission of compressive forces from the femoral component 2 to the tibial component 1 but also as a stop which prevents the tibial component 1 and the femoral component 2 from being pivoted relative to one another from the straightened position towards the front of the knee.

Each of the bearing members 34 and 35 has a hoof-shaped bearing portion such as that identified by the reference numeral 27 in FIG. 5. The bearing portions 27 are provided with the openings 30 which receive the hinge pin 19. The bearing member 34 further includes a lateral portion 28 while the bearing member 35 further includes a lateral portion 29. The lateral portions 28 and 29 have respective sliding surfaces 28A and 29A and each of the sliding surfaces 28A and 29A engages one of the bearing surfaces 17 of the support 8.

The configuration of the bearing portions 27 corresponds to the shape of the condyle which constitutes the femoral bearing element in the natural knee joint. In this regard, FIG. 5 illustrates that each of the bearing portions 27 includes a section 37 which has a relatively large radius and engages a bearing surface 17 of the support 8 when the prosthesis is in its straightened position. In conformance to the shape of the condyle, the section 37 merges smoothly into another section 39 which is located behind the section 37 as considered in a direction from the front of the knee towards the back, that is, which lies in that region of the joint defining the popliteal cavity. The section 39 has a smaller radius than the section 37 and moves into engagement with the bearing surface 17 as the tibial component 1 and the femoral component 2 are pivoted relative to one another about the hinge pin 19. The section 39 merges continuously into an additional section 40 which has a larger radius than the section 39 and constitutes part of the rear portion of the femoral component 2.

The design of the bearing portions 27 is such that the tibial component 1 and the femoral component 2 are forced away from one another when the prosthesis is sharply bent. The resulting elongation of the prosthesis causes the extensors surrounding the prosthesis to be prestressed. Due to the prestressing of the extensors, the prosthesis is damped as it moves into its position of greatest bending. Elongation of the prosthesis is made possible by the fact that the projection 13 is slidable in the synthetic plastic sheath 18 and the fact that the tibial component 1 and the femoral component 2 are unconnected, that is, are not mechanically held together by fasteners. When the prosthesis elongates, the distance between the support 8 and the pivot axis defined by the hinge pin 19 increases. Consequently, more space becomes available in the popliteal cavity for the soft tissue surrounding the prosthesis. Furthermore, the prestressing of the extensors caused by elongation of the prosthesis prevents the rear portions of the tibial component 1 and the femoral component 2 from making hard contact when the prosthesis is sharply bent. This eliminates, or at least greatly reduces, the possibility of breakage.

With reference to FIG. 4, it may be seen that the sliding surfaces 28A and 29A of the lateral portions 28 and 29 continue into the respective bearing portions 27. It may be further observed that the sliding surfaces 28A and 29A are curved in a direction transversely of the lateral portions 28 and 29 or, in other words, transversely of the direction of movement of the lateral portions 28 and 29 during pivoting of the tibial component 1 and the femoral component 2 relative to one another about the hinge 19. The curvature of the sliding surfaces 28A and 29A corresponds at least approximately to that of the bearing surfaces 17 on which they slide and is such that the sliding surfaces 28A and 29A are inclined relative to one another.

The radius of curvature of the sliding surfaces 28A and 29A varies longitudinally of the same. With reference to FIG. 5, the radius of curvature is smallest in the regions of the respective sections 37 which engage the bearing surfaces 17 in the straightened position of the prosthesis. The minimum radius of curvature of the sliding surfaces 28A and 29A essentially equals the radius of curvature of the bearing surfaces 17. The radius of curvature of the sliding surfaces 28A and 29A increases continuously in a direction from the section 37 towards the section 40.

In the straightened position of the prosthesis, the portions of the sliding surfaces 28A and 29A having the smallest radius of curvature are in engagement with the bearing surfaces 17. Since the smallest radius of curvature of the sliding surfaces 28A and 29A essentially equals the radius of curvature of the bearing surfaces 17, these portions of the sliding surfaces 28A and 29A are in full contact with the bearing surfaces 17. Accordingly, when the weight of a user is applied to the prosthesis, the tibial component 1 and the femoral component 2 are largely stabilized against relative movement about the pivot axis defined by the hinge pin 19 under the influence of the resulting compressive forces and the tensile forces in the soft tissue surrounding the prosthesis. Furthermore, in the straightened position of the prosthesis, the portions of the sliding surfaces 28A and 29A having the smallest radius of curvature lock the tibial component 1 and the femoral component 2 against relative rotation about the rotational axis defined by the projection 13.

As indicated previously, the radius of curvature of the sliding surfaces 28A and 29A increases continuously from that of the bearing surfaces 17. Thus, a gap is defined between the bearing surfaces 17 and those portions of the sliding surfaces 28A and 29A having a radius of curvature larger than the same. As the prosthesis is bent or, in other words, as the tibial component 1 and the femoral component 2 are pivoted relative to one another about the hinge pin 19, the size of the gap increases continuously since the radius of curvature of the sliding surfaces 28A and 29A increases continuously and since the manner in which the sliding surfaces 28A and 29A are guided is independent of the degree of bending. In addition, the portions of the sliding surfaces 28A and 29A having the smallest radius of curvature move out of engagement with the bearing surfaces 17 as the prosthesis is bent. As a result of such disengagement and the presence of the gap, the tibial component 1 and the femoral component 2 are able to undergo a limited amount of rotation relative to one another about the rotational axis defined by the projection 13. The projection 13 guides the femoral component 2 with respect to the tibial component 1 during relative rotation of the tibial component 1 and the femoral component 2.

As most clearly shown in FIGS. 3 and 4, the hinge pin 19 is surrounded by a sleeve 42. The sleeve 42 has a tubular extension 54 which is aligned with the recess 20 in the hinge pin 19 and surrounds the sheath 18 in the region below the hinge pin 19. The tubular extension 54 abuts a lip 55 provided at the lower end of the sheath 18.

Figure 10:
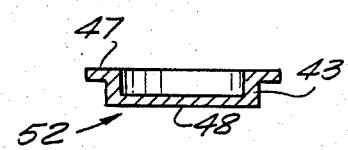
FIG. 10 is a longitudinal cross-sectional view of one embodiment of a mounting member for the hinge pin of the prosthesis according to the invention.

FIG. 4 further illustrates that the hinge pin 19 is mounted in the openings 30 of the bearing members 34 and 35 by means of hat-shaped mounting members 52 and 53. The mounting member 52 is illustrated in FIG. 10 and includes a tubular portion 43 which is received in the opening 30 of the bearing member 34 and accommodates an end portion 44 of the hinge pin 19. A rim 47 is provided at the inner end of the mounting member 52, that is, at the end of the mounting member 52 nearest the mounting member 53, and bears against the surface of the bearing member 34 which faces the bearing member 35. The rim 47 prevents the mounting member 52 from falling out of the opening 30 or, in other words, prevents movement of the mounting member 52 away from the mounting member 53 in a direction along the pivot axis defined by the hinge pin 19. The end of the tubular portion 43 opposite that with the rim 47 is provided with a cover or end wall 48 which is of one piece with the tubular portion 43.

Figure 11:
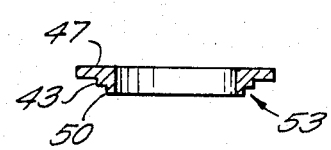
FIG. 11 is a longitudinal cross-sectional view of another embodiment of a mounting member for the hinge pin.
Figure 12:
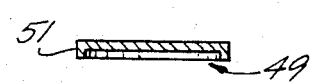
FIG. 12 is a longitudinal cross-sectional view of a cap for the mounting member of FIG. 11.

The mounting member 53 is illustrated in FIGS. 11 and 12. As is the case for the mounting member 52, the mounting member 53 has a tubular portion 43 which is received in the opening 30 of the bearing member 35 and accommodates an end portion 45 of the hinge pin 19. Similarly to the mounting member 52, the tubular portion 43 of the mounting member 53 is provided with a rim 47 which is arranged at its inner end and bears against the surface of the bearing member 35 facing the bearing member 34. As before, the rim 47 of the mounting member 53 confines the latter against movement away from the mounting member 52 in a direction along the pivot axis defined by the hinge pin 19. In contrast to the mounting member 52, the tubular portion 43 of the mounting member 53 is stepped so as to form a protrusion 50 at the end of the tubular portion 43 opposite that with the rim 47. The protrusion 50 is designed to form a snap fit with a corresponding protrusion 51 provided on a cover or end wall 49 which is designed to be releasably engageable with the tubular portion 43 of the mounting member 53. The tubular protrusion 50 on the tubular portion 43 may be replaced by one or more recesses while the tubular protrusion 51 may be replaced by one or more projections designed to be securely engaged by the recess or recesses.

The mounting members 52 and 53 support the hinge pin 19 in such a manner that the covers 48 and 49 bear against the respective end portions 44 and 45 of the hinge pin 19.

Referring once more to FIG. 5, it may be seen that the plate 33 which carries the bearing members 34 and 35 is formed with an arcuate cutout 36. The cutout 36 ensures that a gap exists between the plate 33 and the sleeve 42 which accommodates the hinge pin 19. This prevents any interference with relative pivotal movement of the tibial component 1 and the femoral component 2 about the pivot axis defined by the hinge pin 19.

The prosthesis is implanted by first placing the tibial component 1 in the tibia 9 and the femoral component 2 in the femur 26. The sheath 18, the hinge pin 19, the sleeve 42 and the mounting members 52 and 53 are not installed at this time. The tibial component 1 and the femoral component 2 are initially so arranged relative to one another that the free end of the projection 13 is located below the bearing members 34 and 35.

The mounting member 52 is now inserted in the opening 30 of the bearing member 34. The cover 48 of the mounting member 52 closes this opening 30. Subsequently, the mounting member 53 is inserted in the opening 30 of the bearing member 35 without the cover 49.

The sleeve 42 is next placed between the bearing members 34 and 35 and its internal passage aligned with the openings 30. The hinge pin 19 is then slid into the sleeve 42 and the mounting members 52 and 53 via the exposed opening 30 in the mounting member 35. Once the end portions 44 and 45 of the hinge pin 19 are accommodated in the tubular portions 43 of the mounting members 52 and 53, the opening 30 in the bearing member 35 is closed by placing the cover 49 on the mounting member 53.

The tubular extension 54 of the sleeve 42 is brought into register with the recess 20 in the hinge 19. The sheath 18 is then inserted into the recess 20 via the tubular extension 54. The sheath 18 is now rotated into alignment with the projection 13. The tibial component 1 and the femoral component 2 are then moved relative to and in a direction towards one another so that the projection 13 enters the sheath 18. Once the projection 13 is received in the sheath 18, the projection 13 is capable of performing the function of maintaining the hinge pin 19 in requisite position.

A significant advantage of the prosthesis according to the invention resides in that it may be constructed from easily assembled elements without any screw connections. This advantage is due in large measure to the positioning function performed by the projection 13. The projection 13 further functions to transmit forces between the femoral component 2 and the tibial component 1 in an optimum manner.

The sheath 18 as well as the sleeve 42 and the mounting members 52 and 53 are advantageously composed of a wear-resistant synthetic plastic material. The hinge pin 19 and the projection 13, on the other hand, are favorably composed of a high-strength steel.

The projection 13 is able to slide relative to the sheath 18. When the prosthesis is sharply bent, the projection 13 slides longitudinally relative to the sheath 18 and the femoral component 2 and tibial component 1 move away from one another. Rotational movements of the projection 13 relative to the sheath 18 are possible when the prosthesis is bent so that the portions of the sliding surfaces 28A and 29A having the smallest radius of curvature are out of engagement with the bearing surfaces 17.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contributions to the art and, therefore, such adaptations should and are intended to be comprehended within the meaning and range of equivalence of the appended claims. We claim:

1. An articulated prosthesis, particularly an internal prosthesis, comprising:
   (a) a pair of components arranged to be situated on opposite sides of a joint and to engage corresponding parts of the anatomy;
   (b) a hinge on one of said components for permitting pivotal movement of said components relative to one another about a first axis, said hinge including a hinge pin which is guided by the other of said components so as to permit relative rotation of the latter and said pin about a second axis transverse to said first axis; and
   (c) a pair of mounting members on said one component which are spaced in the direction of said first axis and are arranged to support said pin, said one component being provided with a pair of openings for supporting said mounting members, and each of the latter including a tubular mounting section which is received in the respective opening and accommodates a portion of said pin, each of said mounting members further including a rim extending radially of said first axis, and said rims bearing against said one component to thereby prevent movement of said mounting members away from one another in the direction of said first axis.

2. A prosthesis as defined in claim 1, wherein said one component comprises a pair of bearing members arranged to engage said other component so as to permit compressive stresses to be transmitted between said components, said bearing members being spaced from one another in the direction of said first axis and being provided with said openings.

3. A prosthesis as defined in claim 1, wherein said other component comprises a rod-like projection which is arranged on said second axis and guides said pin so as to permit relative rotation of the latter and said other component about said second axis, said rims being arranged on opposite sides of said projection as considered in the direction of said first axis and closely flanking said projection.

4. A prosthesis as defined in claim 1, wherein each of said mounting members further includes an end wall for positioning said pin in the direction of said first axis.

5. A prosthesis as defined in claim 4, wherein at least one of said end walls is fast with the respective tubular mounting section.

6. A prosthesis as defined in claim 4, wherein at least one of said end walls is releasably connected with the respective tubular mounting section.

7. An articulated prosthesis, particularly an internal prosthesis, comprising:
   (a) a pair of components arranged to be situated on opposite sides of a joint and to engage corresponding parts of the anatomy;
   (b) a hinge on one of said components for permitting pivotal movement of said components relative to one another about a first axis, said hinge including a hinge pin which is guided by the other of said components so as to permit relative rotation of the latter and said pin about a second axis transverse to said first axis; and
   (c) a pair of mounting members on said one component which are spaced in the direction of said first axis and are arranged to support said pin, said one component being provided with a pair of openings for supporting said mounting members, and each of the latter including a tubular mounting section which is received in the respective opening and accommodates a portion of said pin, each of said mounting members further including an end wall for positioning said pin in the direction of said first axis, and each of tubular mounting sections having a pair of opposite ends as considered in the direction of said first axis, each of said end walls being arranged at one end of the respective tubular mounting section, and each of said mounting members also including a rim at the other end of the respective tubular mounting section, said rims extending radially of said first axis and being against said one component to thereby prevent movement of said mounting members away from one another in the direction of said first axis.

8. An articulated prosthesis, particularly an internal prosthesis, comprising:
 (a) a pair of components arranged to be situated on opposite sides of a joint and to engage corresponding parts of the anatomy;
 (b) a hinge on one of said components for permitting pivotal movement of said components relative to one another about a first axis, said hinge including a hinge pin which is guided by the other of said components so as to permit relative rotation of the latter and said pin about a second axis transverse to said first axis; and
 (c) a pair of mounting members on said one component which are spaced in the direction of said first axis and are arranged to support said pin, said mounting members being confined against movement away from one another in the direction of said first axis, and said one component being provided with a pair of openings for supporting said mounting members, each of the latter including a tubular mounting section which is received in the respective opening and accommodates a portion of said pin, and each of said mounting members further including an end wall for positioning said pin in the direction of said first axis, at least one of said end walls being of one piece with the respective tubular mounting section.

9. An articulated prosthesis, particularly an internal prosthesis, comprising:
 (a) a pair of components arranged to be situated on opposite sides of a joint and to engage corresponding parts of the anatomy;
 (b) a hinge on one of said components for permitting pivotal movement of said component relative to one another about a first axis, said hinge including a hinge pin which is guided by the other of said components so as to permit relative rotation of the latter and said pin about a second axis transverse to said first axis; and
 (c) a pair or mounting members on said one component which are spaced in the direction of said first axis and are arranged to support said pin, said mounting members being confined against movement away from one another in the direction of said first axis, and said one component being provided with a pair of openings for supporting said mounting members, each of the latter including a tubular mounting section which is received in the respective opening and accommodates a portion of said pin, and each of said mounting members further including an end wall for positioning said pin in the direction of said first axis, at least one of said end walls and the respective tubular mounting section being connected by a snap fit.

* * * * *